US011344054B2

(12) United States Patent
Dardelle et al.

(10) Patent No.: US 11,344,054 B2
(45) Date of Patent: May 31, 2022

(54) PROCESS FOR DRYING A SUSPENSION OF HYDROGEL MICROCAPSULES

(71) Applicant: Firmenich SA, Satigny (CH)

(72) Inventors: Gregory Dardelle, Meyrin (CH); Amal Elabbadi, Meyrin (CH); Pierre-Etienne Bouquerand, Meyrin (CH); Philipp Erni, Meyrin (CH)

(73) Assignee: Firmenich SA, Satigny (CH)

(*) Notice: Subject to any disclaimer, the term of this patent is extended or adjusted under 35 U.S.C. 154(b) by 0 days.

(21) Appl. No.: 16/633,742

(22) PCT Filed: Jul. 24, 2018

(86) PCT No.: PCT/EP2018/070063
§ 371 (c)(1),
(2) Date: Jan. 24, 2020

(87) PCT Pub. No.: WO2019/020642
PCT Pub. Date: Jan. 31, 2019

(65) Prior Publication Data
US 2020/0229483 A1    Jul. 23, 2020

(30) Foreign Application Priority Data
Jul. 27, 2017 (EP) .................................... 17183449

(51) Int. Cl.
| A23P 10/30 | (2016.01) |
| A23L 27/00 | (2016.01) |
| A23L 2/56 | (2006.01) |
| B01J 13/14 | (2006.01) |
| B01J 13/20 | (2006.01) |

(52) U.S. Cl.
CPC ................. *A23P 10/30* (2016.08); *A23L 2/56* (2013.01); *A23L 27/72* (2016.08); *B01J 13/14* (2013.01); *B01J 13/206* (2013.01); *A23V 2002/00* (2013.01)

(58) Field of Classification Search
CPC .. A23P 10/30; A23L 27/72; A23L 2/56; B01J 13/14; B01J 13/206; B01J 13/0069; B01J 13/20; A23V 2002/00; A01N 25/28; A61K 8/11
See application file for complete search history.

(56) References Cited

U.S. PATENT DOCUMENTS

| 5,093,130 | A | * | 3/1992 | Fujii ........................ | A01C 1/06 |
| | | | | | 424/195.18 |
| 5,204,029 | A | * | 4/1993 | Morgan .................... | B01J 13/04 |
| | | | | | 264/4.4 |
| 2008/0155853 | A1 | * | 7/2008 | Wang ........................ | B01J 2/04 |
| | | | | | 34/285 |
| 2008/0206325 | A1 | * | 8/2008 | Bouquerand ........ | A61K 9/5073 |
| | | | | | 424/463 |
| 2011/0117180 | A1 | * | 5/2011 | Yan ......................... | A23L 33/12 |
| | | | | | 424/450 |
| 2013/0302392 | A1 | * | 11/2013 | Mistry .................... | C09K 15/00 |
| | | | | | 424/401 |
| 2015/0272897 | A1 | * | 10/2015 | Ollagnier ............... | A61Q 17/04 |
| | | | | | 424/451 |

FOREIGN PATENT DOCUMENTS

| FR | 2996466 A1 | 4/2014 |
| WO | 9917871 A1 | 4/1999 |
| WO | 2009111684 A1 | 9/2009 |
| WO | 2012122010 A2 | 9/2012 |
| WO | 2012168144 A1 | 12/2012 |
| WO | 2014044840 A1 | 3/2014 |
| WO | 2016124746 A1 | 8/2016 |
| WO | 2016162381 A1 | 10/2016 |

OTHER PUBLICATIONS

International Search Report and Written Opinion for International Patent Application No. PCT/EP2018/070063, dated Aug. 21, 2018, 11 pages.

* cited by examiner

*Primary Examiner* — Monica A Shin
(74) *Attorney, Agent, or Firm* — Armstrong Teasdale LLP (57) ABSTRACT

Described herein is a new process for the preparation of powdered microcapsules encapsulating active volatile active ingredients, in particular a perfume or a flavour, the process being performed at room temperature. Powdered microcapsules obtainable by the process are also described. Perfuming and flavouring compositions as well as consumer products including the capsules are also described.

11 Claims, 2 Drawing Sheets

PROCESS FOR DRYING A SUSPENSION OF HYDROGEL MICROCAPSULES

CROSS-REFERENCE TO RELATED APPLICATIONS

This application is a National Stage Application of International Patent Application No. PCT/EP2018/070063, filed Jul. 24, 2018, which claims the benefit of priority to European Patent Application No. 17183449.2, filed Jul. 27, 2017, the entire contents of which are hereby incorporated by reference herein.

TECHNICAL FIELD

The present invention relates to the field of delivery systems. More particularly, the invention pertains to a process for the preparation of dried microcapsules encapsulating active volatile ingredients, in particular a perfume or a flavour. The process of the invention provides an advantageous sustainable alternative to spray-drying or to fluid bed drying as it takes place at room temperature or below. Dried microcapsules obtainable by said process are also an object of the invention. Perfuming and flavouring compositions as well as consumer products comprising said microcapsules are also part of the invention.

BACKGROUND OF THE INVENTION

One of the problems faced by the perfume and flavour industry lies in the relatively rapid loss of olfactive benefit provided by active compounds due to their volatility, particularly that of "top-notes". The encapsulation of those active substances provides at the same time a protection of the ingredients there-encapsulated against "aggressions" such as oxidation or moisture and allows, on the other hand, a certain control of the kinetics of flavour or fragrance release to induce sensory effects through sequential release.

Spray-drying is part of the most common techniques used to stabilise volatile substances such as flavours and fragrances by encapsulating them in a solid form, suited to many applications. Spray-drying can be used to transform a simple emulsion into a powder, therefore providing an encapsulated system in the form of a matrix, but has also been described as a suitable technique to dry aqueous suspension of microcapsules.

Spray-dried powders are commonly made by spraying liquid emulsions or slurries or suspensions into a stream of hot air. Spray-drying is usually done by means of a rotating disc or of multicomponent nozzles. Detailed techniques are described for instance in K. Masters, Spray-drying Handbook, Longman Scientific and Technical 1991. This drying technique suffers from several drawbacks, the main one being the temperature at which the process is performed, which necessarily leads to volatile losses during the process. Another related problem is that of technical safety, the above-described encapsulation equipment suffering from explosions of particles suspended in the air. The problem of reducing the violence of possible explosion has therefore to be addressed, e.g. by using particular fireproofing agents in formulations.

Solutions to address the problem of reducing volatile losses during spray-drying have been described, among which spray-drying at lower temperatures. WO2012/122010 describes in particular a solution based on a modification of the equipment to have an inlet temperature of less than 100° C. and an air inlet dew point comprised between −10° C. and +5° C. in order to preserve volatiles during the process. However, besides the costs generated by the equipment, this process still generates volatile losses.

Furthermore, spray-drying is not suitable to dry microcapsules having a large particle size. To address this problem, fluid bed drying is a known technique to dry microcapsules, even with a large particle size. However, this technique involves heat leading to volatile losses as already explained previously for the spray-drying. Moreover, this process requires a complex equipment.

There is therefore a need to find an alternative solution to existing drying techniques with the purpose of drying microcapsule slurries to form a dried free-flowing microcapsules powder while preserving the active volatiles to be encapsulated. The present invention solves this problem by providing a simple and cost-effective process taking place at room temperature or below which allows to efficiently dry a suspension of hydrogel microcapsules encapsulating an oil phase.

SUMMARY OF THE INVENTION

The process of the invention performed at room temperature or below allows preparing dried microencapsulated systems while preserving the volatile ingredients there-encapsulated.

The process disclosed therefore allows to form dry microcapsules while retaining the process temperature low enough to significantly reduce evaporative losses of the volatile actives during the process.

A first object of the invention is a process for drying at room temperature or below room temperature a suspension of hydrogel microcapsules, said method comprising the steps of:
 (i) providing an aqueous suspension of hydrogel microcapsules, each microcapsule comprising an oil phase containing a hydrophobic active ingredient, preferably a perfume or a flavor; wherein the weight ratio between microcapsules and water is preferably above 0.8;
 (ii) mixing the suspension obtained in step (i) with hydrophobic particles to obtain free-flowing microcapsules;
 (iii) drying the free-flowing microcapsules obtained in step (ii) by mixing the microcapsules with a desiccant and/or by submitting the microcapsules under a gas flow to obtain a dried free-flowing microcapsules powder; and
 (iv) optionally, sifting the dried microcapsules powder to remove the excess desiccant.

In a second aspect, the invention relates to dried microcapsules, preferably perfuming or flavouring dried microcapsules, obtainable by a process as defined above.

In a third aspect, the invention concerns a perfuming or flavouring composition comprising
 (i) perfuming or flavouring dried microcapsules as defined above; and
 (ii) at least one perfuming or flavouring co-ingredient.

In a fourth and fifth aspects, the invention relates to perfumed consumer products and flavoured edible products comprising the dried microcapsules defined above.

DETAILED DESCRIPTION OF THE INVENTION

Unless stated otherwise, percentages (%) are meant to designate a percentage by weight of a composition.

By "room temperature" it is meant a temperature typically comprised between 20° C. and 30° C.

By "below room temperature" it is meant a temperature typically comprised between −30° C. and 20° C.; such temperature can be achieved by the use of a cooling chamber or a refrigeration room.

According to an embodiment, the process is carried out at a temperature comprised between −30° C. and 30° C.

By "perfume or flavour oil", it is meant a single perfuming or flavouring compound or a mixture of several perfuming or flavouring compounds.

For the sake of clarity, the expression "suspension" in the present invention is meant to designate a system in which microcapsules are dispersed in an aqueous continuous phase.

By "hydrogel microcapsules", it is meant that the main component constituting the microcapsule (shell or carrier) is a hydrated polymeric network. The morphology of the hydrogel microcapsules of the invention can vary from a core-shell to a matrix type.

According to one embodiment, it is of the core-shell type. In this case, the microcapsules comprise an oil-based core, and a hydrogel shell.

By "free-flowing microcapsules", it is meant single, individual, discrete microcapsules that are not agglomerated.

The present invention provides an advantageous alternative to powders dried by spray-drying or fluid bed drying with a simplified and cost-effective process involving no heating and performed at room temperature or below while still providing an efficient oil encapsulation.

Furthermore, individual microcapsules without agglomeration and with specific properties such as thermal release can be prepared according to the process of the invention.

The present invention therefore relates in a first aspect to a process for drying at room temperature or below room temperature a suspension of hydrogel microcapsules, said method comprising the steps of:
(i) providing an aqueous suspension of hydrogel microcapsules, each microcapsule comprising an oil phase containing a hydrophobic active ingredient, preferably a perfume or a flavor; wherein the weight ratio between microcapsules and water is preferably above 0.8;
(ii) mixing the suspension obtained in step (i) with hydrophobic particles to obtain free-flowing microcapsules;
(iii) drying the free-flowing microcapsules obtained in step (ii) by mixing the microcapsules with a desiccant and/or by submitting the microcapsules under a gas flow to obtain a dried free-flowing microcapsules powder; and
(iv) optionally, sifting the dried microcapsules powder to remove the excess desiccant.

According to the invention, the whole process is free of any spray-drying step or free of any fluid bed drying and is performed at room temperature or below room temperature.

According to an embodiment, the process for drying is carried out at room temperature.

The process according to the invention provides over traditional drying methods the advantage of reducing possible volatile losses and respecting the initial liquid olfactory or flavour profile. It is also a way of reducing the production costs and carbon footprint, and it avoids explosion risks associated with drying liquids in hot air.

$1^{st}$ Step: Providing an Aqueous Suspension of Hydrogel Microcapsules

In a first step of the process, an aqueous suspension of hydrogel microcapsules is provided.

Hydrogel microcapsules defined in the present invention can be obtained by any process known in the art and do not necessitate a more detailed description. As non-limiting examples, those microcapsules can be obtained by a process selected from the group consisting of simple coacervation, complex coacervation, prilling, interfacial polymerization or a combination thereof.

According to a particular embodiment the microcapsules have a core-shell structure with a hydrogel shell.

According to another embodiment, the microcapsules have a hydrogel shell resulting from complex coacervation wherein the shell is possibly cross-linked such as described in WO2014044840.

In preferred embodiments of the invention, the shell/membrane of the coacervate capsule of the invention comprises two coacervated polymers, a first polymer ("polymer 1") and a second polymer ("polymer 2").

In some preferred embodiments, the first polymer, polymer 1, is a protein or a polypeptide capable of adsorbing at the surface of the particles to form a new complex that is positively or negatively charged. Proteins suitable for coacervation processes are gelatins and albumins; proteins from pea, potato, wheat; globulins from vegetable, animal or microbial sources.

In some preferred embodiment, the second polymer, polymer 2, is a non-protein polymer charged oppositely to the protein of the first polymer, polymer 1, in the range of pH values that are known to be of interest for coacervation. These non-protein polymers include gum Arabic (also known as Acacia gum or gum acacia) and similar plant gums, gum tragacanth, CARBOPOL® poly(acrylic acid), low methoxy pectin, xanthan gum, sodium carboxymethyl guar gum, guar gum, high methoxyl pectin, carboxymethyl cellulose (CMC), alginates, carrageenans (including kappa-carrageenan, iota-carrageenan, lambda-carrageenan and mixtures thereof), dextrane sulfate, polyphosphates (e.g., sodium hexametaphosphates), or microbial exopolysaccharides. Details on the characteristics of suitable polymers can be found in the scientific literature on coacervation and on polyelectrolyte complexes (for example, in de Kruif C. G., Weinbreck F., de Vries R., Current Opinion in Colloid & Interface Science 9:340-349, 2004).

Preferably, the second polymer, polymer 2, is chosen among the group of weakly anionic polyelectrolytes including gum arabic and similar plant gums, carboxymethyl cellulose, low methoxy pectin, carbopol, sodium carboxymethyl guar gum, and alginates.

Most preferably, the second polymer, polymer 2, is negatively charged when the pH is greater than 2. In one preferred embodiment, the second polymer, polymer 2, is gum Arabic.

Suitable agents for cross-linking include, but are not limited to, formaldehyde, acetaldehyde, glutaraldehyde, glyoxal, chrome alum, tannic acid and transglutaminase. The enzyme transglutaminase, which is readily available commercially (e.g., from Ajinomoto Corp., Japan), is preferably used at 10-100 activity units per gram of the first polymer, for example, gelatin, and most preferably at 30-60 activity units per gram of the first polymer.

According to a particular embodiment, the hydrogel shell of microcapsules is not cross-linked. Indeed, one advantage of the process of the invention is that the shell does not need to be cross-linked since no heating is involved in this process. Consequently, according to this embodiment, microcapsules dried by the process of the invention can release flavor or fragrance by thermal trigger.

The microcapsules have preferably a mean diameter greater than 100 µm, preferably greater than 200 µm.

According to an embodiment, the aqueous suspension is free from a water-soluble carbohydrate.

The microcapsules defined in the present invention comprising an oil phase including a hydrophobic active ingredient.

According to a particular embodiment, botanic tissues are not encapsulated in the hydrogel microcapsules.

According to a preferred embodiment, the active ingredient consists of a perfume or flavour. Alternative hydrophobic ingredients which could benefit from being encapsulated could be used either instead of a perfume or flavour, or in combination with a perfume or flavour. Non-limiting examples of such ingredients include a cosmetic, skin caring, malodour counteracting, bactericide, fungicide, pharmaceutical or agrochemical ingredient, a sanitizing agent, an insect repellent or attractant.

By "perfume oil" (or also "perfume") or "flavour" what is meant here is an ingredient or composition that is a liquid at about 20° C. Said perfume or flavour oil can be a perfuming or flavouring ingredient alone or a mixture of ingredients in the form of a perfuming or flavouring composition. As a "perfuming ingredient" it is meant here a compound, which is used in perfuming preparations or compositions to impart as primary purpose a hedonic effect. In other words such an ingredient, to be considered as being a perfuming one, must be recognized by a person skilled in the art as being able to at least impart or modify in a positive or pleasant way the odor of a composition, and not just as having an odor. The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

By "flavour ingredient or composition" it is meant here a flavouring ingredient or a mixture of flavouring ingredients, solvent or adjuvants of current use for the preparation of a flavouring formulation, i.e. a particular mixture of ingredients which is intended to be added to an edible composition or chewable product to impart, improve or modify its organoleptic properties, in particular its flavour and/or taste. Taste modulator as also encompassed in said definition. Flavouring ingredients are well known to a skilled person in the art and their nature does not warrant a detailed description here, which in any case would not be exhaustive, the skilled flavourist being able to select them on the basis of his general knowledge and according to the intended use or application and the organoleptic effect it is desired to achieve. Many of these flavouring ingredients are listed in reference texts such as in the book by S. Arctander, Perfume and Flavor Chemicals, 1969, Montclair, N.J., USA, or its more recent versions, or in other works of similar nature such as Fenaroli's Handbook of Flavor Ingredients, 1975, CRC Press or Synthetic Food Adjuncts, 1947, by M. B. Jacobs, can Nostrand Co., Inc. Solvents and adjuvants or current use for the preparation of a flavouring formulation are also well known in the art.

In a particular embodiment, the flavour is selected from the group consisting of terpenic flavours including citrus and mint oil, and sulfury flavours.

According to any one of the invention's embodiment, the oil represents between about 10% and 60% w/w, or even between 20% and 50% w/w, by weight, relative to the total weight of the suspension.

According to the invention, it is preferable to provide an aqueous suspension with a low water content as it impacts the concentration of hydrophobic particles needed in step (ii) as well as the efficiency of step (ii) and affects also the concentration of desiccant in step (iii) required to dry the microcapsules.

Thus, according to an embodiment, the weight ratio between microcapsules and water is preferably above 0.8, preferably above 1.

In other words, the water content in the aqueous suspension in step (i) is preferably not above 55% by weight, preferably not above 50% by weight based on the total weight of the suspension.

The aqueous suspension in step (i) is typically in the form of a viscous suspension (like a paste).

The person skilled in the art will be able to adjust the water content by using common methods of concentration (for example a combination of decantation, draining and vacuum filtration).

Second Step (ii): Mixing the Suspension Obtained in Step (i) with Hydrophobic Particles In a second step of the process of the invention, the suspension obtained in step (i) is mixed with hydrophobic particles.

This step is essential in the process of the invention to avoid irreversible particles aggregation and achieve individual and discrete microcapsules upon drying. The target of this step is to transform the suspension of step (i) (that is in the form of a paste)—hardly difficult to handle and dry—into a free flowing system. To that end, hydrophobic particles are mixed into the microcapsules suspension to induce the disruption of the water bridges between hydrogel microcapsules thus dropping away the attractive effect of capillary forces. The product obtained after step (ii) is free flowing microcapsules. At the end of this step, microcapsules are wet.

The Energy/shear required in this step is relatively limited to avoid the rupture of the capsules and minimize volatile losses. The preferred blending process used here is a shaker-mixer. However, of course other blending methods could fit to these requirements.

Hydrophobic particles can be selected from the group consisting of treated silica such as hydrophobic silica or fumed silica, stearates such as magnesium stearate, waxes such as carnauba wax and mixtures thereof.

The ratio between hydrophobic particles and microcapsules is preferably comprised between 0.001 and 0.15, more preferably comprised between 0.01 and 0.10.

Step (iii): Drying the Free-Flowing Microcapsules Obtained in Step (ii) by Mixing the Microcapsules with a Desiccant and/or by Submitting the Microcapsules to a Gas Flow to Obtain a Dried Free-Flowing Microcapsules Powder In a third step of the process of the invention, the free-flowing microcapsules obtained in step (ii) is mixed with a desiccant and/or is submitted to a gas flow, for example air flow, to obtain a dried free-flowing microcapsules powder.

When the process comprises a step of submitting the microcapsules to a gas flow in addition to the desiccant, this step can be carried out before, at the same time or after the addition of the desiccant.

One advantage of this particular embodiment is to reduce the amount of desiccant required for drying the free-flowing microcapsules of step (ii).

Desiccant

According to a particular embodiment, step (iii) consists in drying the free-flowing microcapsules obtained in step (ii) by mixing the microcapsules with a desiccant.

During this step, the drying of the microcapsules shell will occur by water transport from microcapsules shell towards the desiccant. This phenomenon is fully driven by water sorption features of the desiccant.

When present, the desiccant is preferably used in an amount such that weight ratio between desiccant and microcapsules is comprised between 0.1 and 10, preferably between 0.5 and 5 and more preferably between 1 and 4.

Examples of desiccant suitable for the invention include maltodextrin, starch, polyvinyl acetate, polyvinyl alcohol, dextrines, natural or modified starches, vegetable gums, pectins, xanthanes, alginates, carrageenans, cellulose derivatives, gelatins, silicas, clays, activated charcoal, calcium sulfate, calcium chloride, and molecular sieves (zeolites) and mixtures thereof.

The mixing step can be achieved with a simple rotary mixer.

The shear applies during this mixing step is preferably low to avoid the rupture of the capsules and minimize volatile losses.

Gas Flow

In addition or to substitute the use of a desiccant in step (iii), the free-flowing microcapsules obtained in step (ii) can be dried under a gas flow. Typically, the free-flowing microcapsules can be mixed in a rotary pan under gas flow, for example air flow between 30 minutes and 2 hours.

Sifting Step

According to one embodiment of the process of the invention, the obtained free flowing powder is then sifted. Different sieves characterized by different mesh sizes can be used. As an example, sieves with mesh size 1400/800/500/200 µm can be used in the context of the invention.

According to any of the above-described embodiments, a flowing agent can be used in the process of the invention. The flowing agent can ease the separation between the formed microcapsules and the desiccant used to dry the free-flowing microcapsules when there is a sifting step. It can also be used to improve the flowability of the resulting powders in the absence of sifting step. Flowing agents are well-known from the person skilled in the art. As non-limiting example, one may cite for example hydrophilic silica.

According to an embodiment, the process is devoid of a sifting step.

According to an embodiment, any of the process steps mentioned above may be performed at temperature below room temperature, for example, in a cooling chamber or in a refrigeration room.

A second object of the invention consist of perfuming or flavouring powdered microcapsules obtainable by a process as described in any of the above-described embodiments.

The microcapsules according to the invention, present an advantageous alternative to powder dried by spray-drying or by fluid bed drying as they ensure an optimal preservation of the profile from the perfume or flavour there-encapsulated.

Such microcapsules could also be prepared with any other hydrophobic active material as mentioned above.

The products of the invention can be used for the preparation of perfuming or flavouring compositions which are also an object of the invention.

In particular a perfuming composition comprising (i) perfuming powdered microcapsules as defined above; (ii) at least one perfuming co-ingredient; and (iii) optionally a perfumery adjuvant, is another object of the invention.

By "perfuming co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor. The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30% by weight of microcapsules as defined above.

The invention's microcapsules can advantageously be used in all the fields of modern perfumery. Consequently, another object of the present invention is represented by a perfuming consumer product comprising as a perfuming ingredient, the microcapsules defined above or a perfuming composition as defined above.

The invention's microcapsules can therefore be added as such or as part of an invention's perfuming composition in a perfuming consumer product.

Another object of the invention is therefore a perfumed consumer product comprising:
a) from 0.5 to 65% by weight, preferably from 2 to 65% by weight, relative to the total weight of the consumer product, of at least one surfactant;
b) microcapsules as defined above.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises a functional formulation, as well as optionally additional benefit agents, corresponding to the desired consumer product, e.g. a detergent or an air freshener, and an olfactive effective amount of at least one invention's compound.

The nature and type of the constituents of the perfumery consumer product do not warrant a more detailed description here, which in any case would not be exhaustive, the skilled person being able to select them on the basis of his general knowledge and according to the nature and the desired effect of said product. Formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumery consumer product can be a perfume, such as a fine perfume, a cologne or an after-shave lotion; a fabric care product, such as a detergent, tablets and pods, a fabric softener, a dryer sheet, a fabric refresher, an ironing water, or a bleach; a body-care product, such as a hair care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces.

Preferably, the perfuming consumer product comprises from 0.1 to 15 wt %, more preferably between 0.2 and 5 wt % of the microcapsules of the present invention, these percentages being defined by weight relative to the total weight of the consumer product. Of course the above concentrations may be adapted according to the olfactive effect desired in each product.

The microcapsules of the invention when encapsulating a flavour, can also be used in a great variety of edible end products. Consumer products susceptible of being flavoured by the microcapsules of the invention may include foods, beverages, pharmaceutical and the like.

According to an embodiment, the consumer product is obtained by mixing the powdered microcapsules with additional components depending on the nature of the consumer product.

For example foodstuff base that could use the powdered microcapsules of the invention include
Baked goods (e.g. bread, dry biscuits, cakes, other baked goods),
Non-alcoholic beverages (e.g. carbonated soft drinks, bottled waters, sports/energy drinks, juice drinks, vegetable juices, vegetable juice preparations),
Alcoholic beverages (e.g. beer and malt beverages, spirituous beverages),
Instant beverages (e.g. instant vegetable drinks, powdered soft drinks, instant coffee and tea),
Cereal products (e.g. breakfast cereals, pre-cooked ready-made rice products, rice flour products, millet and sorghum products, raw or pre-cooked noodles and pasta products),
Milk products (e.g. fresh cheese, soft cheese, hard cheese, milk drinks, whey, butter, partially or wholly hydrolysed milk protein-containing products, fermented milk products, condensed milk and analogues),
Dairy based products (e.g. fruit or flavored yoghurt, ice cream, fruit ices)
Confectionary products (e.g. chewing gum, hard and soft candy)
Chocolate and compound coatings
Products based on fat and oil or emulsions thereof (e.g. mayonnaise, spreads, margarines, shortenings, remoulade, dressings, spice preparations),
Spiced, marinated or processed fish products (e.g. fish sausage, surimi),
Eggs or egg products (dried egg, egg white, egg yolk, custard),
Desserts (e.g. gelatins and puddings)
Products made of soya protein or other soya bean fractions (e.g. soya milk and products made therefrom, soya lecithin-containing preparations, fermented products such as tofu or tempeh or products manufactured therefrom, soya sauces),
Vegetable preparations (e.g. ketchup, sauces, processed and reconstituted vegetables, dried vegetables, deep frozen vegetables, pre-cooked vegetables, vegetables pickled in vinegar, vegetable concentrates or pastes, cooked vegetables, potato preparations),
Vegetarian meat replacer, vegetarian burger
Spices or spice preparations (e.g. mustard preparations, horseradish preparations), spice mixtures and, in particular seasonings which are used, for example, in the field of snacks.
Snack articles (e.g. baked or fried potato crisps or potato dough products, bread dough products, extrudates based on maize, rice or ground nuts),
Meat products (e.g. processed meat, poultry, beef, pork, ham, fresh sausage or raw meat preparations, spiced or marinated fresh meat or cured meat products, reformed meat),
Ready dishes (e.g. instant noodles, rice, pasta, pizza, tortillas, wraps) and soups and broths (e.g. stock, savory cube, dried soups, instant soups, pre-cooked soups, retorted soups), sauces (instant sauces, dried sauces, ready-made sauces, gravies, sweet sauces).

Preferably, the microcapsules according to the invention shall be used in products selected from the group consisting of baked goods, instant beverages, cereal products, milk products, dairy-based products, products based on fat and oil or emulsions thereof, desserts, vegetable preparations, vegetarian meat replacer, spices and seasonings, snacks, meat products, ready dishes, soups and broths and sauces.

The invention will now be further described by way of examples. It will be appreciated that the invention as claimed is not intended to be limited in any way by these examples.

EXAMPLES

Example 1

Preparation of a Suspension of Core-Shell Microcapsules as Defined in the Present Invention Aqueous solutions of 10% wt. pork gelatine (A) (250 Bloom, supplied by Norland), and 10% wt. gum Arabic (B) (Efficacia®, from CNI), are prepared separately.

In a vessel at 40° C., 25.4 g of solution (A) and 12.7 g of solution (B) are added to 92.8 g of warm demineralised water under mechanical shear. pH is adjusted to 4.5 using HCl 1M. The mixture is maintained at 40° C. during 15 min.

19.1 g of limonene oil is slowly added to the mixture and homogenised at 250 RPM during 5 min, so as to reach an average droplet size of 600 μm. Mechanical shear is maintained while the solution is let to cool down at 10° C. at a rate of 0.3° C.·min-1. The stirring speed is slightly decreased, and 0.102 g of glutaraldehyde (aq. 50% wt. Supplied by Sigma-Aldrich) is added to the mixture. Cross-linking is allowed to proceed during 4 to 10 hours at 20° C. The result is an aqueous suspension of microcapsules (named X).

Example 2

Preparation of a Suspension of Core-Shell Microcapsules as Defined in the Present Invention Solution (A') is an aqueous solution of 10% wt of warm water fish gelatine (230 Bloom, supplied by Wheishardt). In a vessel at 40° C., 25.4 g of solution (A') and 12.7 g of solution (B) (as prepared in example 1) are added to 92.8 g of warm demineralised water under mechanical shear. pH is adjusted to 4.5 using HCl 1M. The mixture is maintained at 40° C. during 15 min.

19.1 g of limonene oil is slowly added to the mixture and homogenised at 250 RPM during 5 min, so as to reach an average droplet size of 600 μm. Mechanical shear is maintained while the solution is let to cool down at 10° C. at a rate of 0.3° C.·min-1. The stirring speed is slightly decreased, the pH is adjusted to 4.5 and 1.01 g of transglutaminase (ACTIVA® WM supplied by Ajinomoto) is added to the mixture. Cross-linking is allowed to proceed during 10 hours at 20° C. The result is an aqueous suspension of microcapsules (named Y).

Example 3

Preparation of a Suspension of Core-Shell Microcapsules as Defined in the Present Invention Solution (A') is an aqueous solution of 10% wt of warm water fish gelatine (230 Bloom, supplied by Wheishardt). In a vessel at 40° C., 25.4 g of solution (A') and 12.7 g of solution (B) (as prepared in example 1) are added to 92.8 g of warm demineralised water under mechanical shear. pH is adjusted to 4.5 using HCl 1M. The mixture is maintained at 40° C. during 15 min.

19.1 g of limonene oil is slowly added to the mixture and homogenised at 250 RPM during 5 min, so as to reach an average droplet size of 600 μm. Mechanical shear is maintained while the solution is let to cool down at 10° C. at a rate of 0.3° C.·min-1. The stirring speed is slightly decreased, the pH is adjusted to 4.5 and 1.01 g of transglutaminase (ACTIVA® WM supplied by Ajinomoto) is added to the mixture. Cross-linking is allowed to proceed during 10 hours at 20° C. The result is an aqueous suspension of microcapsules (named Z).

Example 4

Preparation of a Dried Microcapsules According to the Invention Based on a Suspension of Core-Shell Microcapsules 70 g of the initial aqueous suspension of microcapsules X, Y or Z (prepared according to examples 1-3) is transferred into a separating funnel and concentrated by decantation, 35 g of water is then drained. Finally 14 g of water is removed from the remaining suspension by vacuum filtration, bringing the total water content below 50% w/w. The concentrated suspension obtained at that stage is a paste-like product.

0.21 g of fumed silica (Aerosil® R974 supplied by Evonik) and 21 g of the paste-like product are introduced into a shaker-mixer and allow to mix until obtaining free-flowing microcapsules. The free-flowing microcapsules are then transferred into a rotary pan, 42 g of native starch (desiccant) and 0.021 g of flowing agent (Sipernat® supplied by Evonik) are incorporated into the rotary pan and blended for 1 hour to allow a homogeneous and complete drying of the microcapsules. The resulting powder mixture is then sifted using conventional sieving unit to remove the desiccant and concentrate the product.

Figure 1:
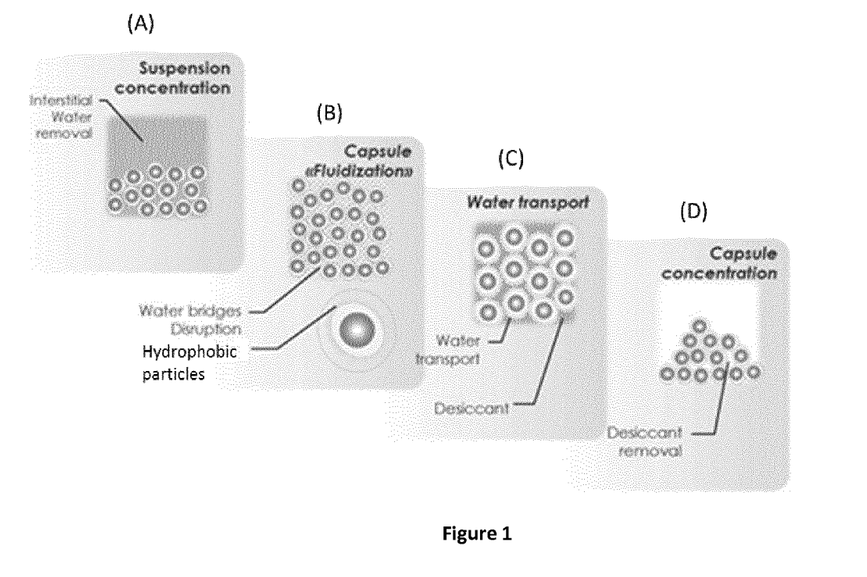
FIG. 1 is a schematic representation of the process according to the invention.
Figure 2:
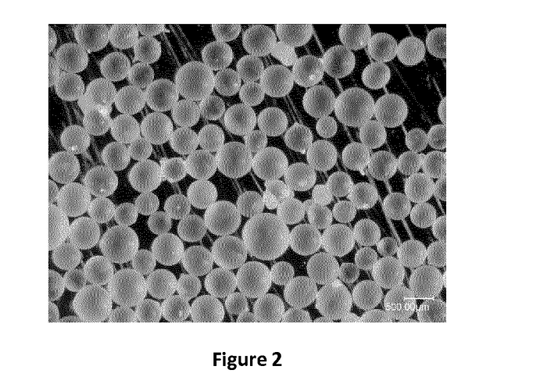
FIG. 2 represents a microscopic observation of dried microcapsules X described in example 4.

A free-flowing dried powder was obtained for the 3 different types of microcapsules (X, Y and Z) (see FIG. 2 for microcapsules X).

According to Low-Field NMR measurements, the perfume oil loading of the final powder obtain according to the present invention is high and reaches approximately 85% w/w.

Example 5

Preparation of a Dried Microcapsules According to the Invention Based on a Suspension of Core-Shell Microcapsules 70 g of the initial aqueous suspension of microcapsules X, Y or Z (prepared according to examples 1-3) is transferred into a separating funnel and concentrated by decantation, 35 g of water is then drained. Finally 14 g of water is removed from the remaining suspension by vacuum filtration, bringing the total water content below 50% w/w. The concentrated suspension obtained at that stage is a paste-like product.

1.3 g of magnesium stearate (technical grade Supplied by Sigma-Aldrich) and 21 g of the paste-like product are introduced into a shaker-mixer and allowed to mix until obtaining free-flowing microcapsules. The free-flowing microcapsules are then transferred into a rotary pan, and 66.8 g of native starch (desiccant) are incorporated into the rotary pan and blended for 1 hour to allow a homogeneous and complete drying of the microcapsules. The resulting powder mixture is then sifted using conventional sieving unit to remove the desiccant and concentrate the product.

Figure 3:
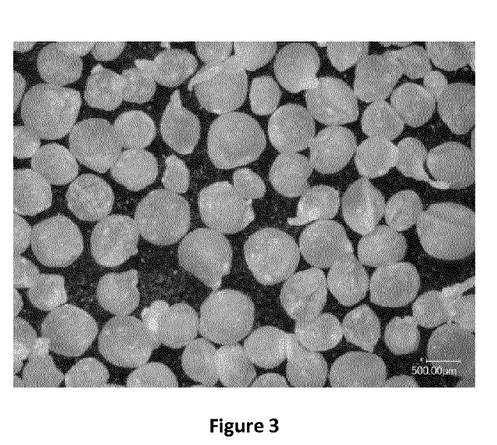
FIG. 3 represents a microscopic observation of dried microcapsules Y described in example 5.
Figure 4:
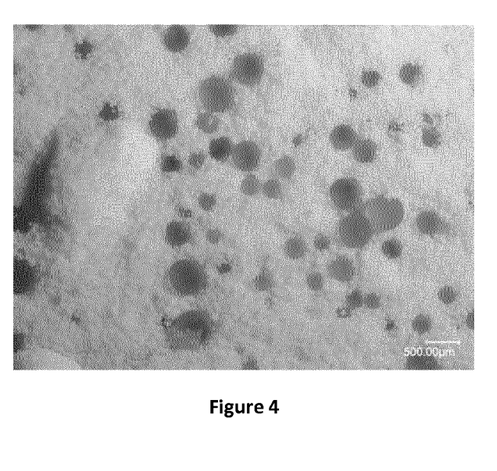
FIG. 4 represents a microscopic observation of dried microcapsules X described in example 7.

A free-flowing dried powder was obtained for the 3 different types of microcapsules (X, Y and Z) (see FIG. 3 for microcapsules Y).

According to Low-Field NMR measurements, the perfume oil loading of the final powder reaches approximately 85% w/w.

Example 6

Preparation of a Dried Microcapsules According to the Invention Based on a Suspension of Core-Shell Microcapsules 70 g of the initial aqueous suspension of microcapsules X, Y or Z (prepared according to examples 1-3) is transferred into a separating funnel and concentrated by decantation, 35 g of water is then drained. Finally 14 g of water is removed from the remaining suspension by vacuum filtration, bringing the total water content below 50% w/w. The concentrated suspension obtained at that stage is a paste-like product.

2.1 g of micronized carnauba wax (MicroKlear 418 Supplied by MicroPowder Inc.) and 21 g of the paste-like product are introduced into a shaker-mixer and allowed to mix until obtaining free-flowing microcapsules. The free-flowing microcapsules are then transferred into a rotary pan, 42 g of native starch (desiccant) and 0.021 g of flowing agent (Sipernat® supplied by Evonik) are incorporated into the rotary pan and blended for 1 hour to allow a homogeneous and complete drying of the microcapsules. The resulting powder mixture is then sifted using conventional sieving unit to remove the desiccant and concentrate the product.

A free-flowing dried powder was obtained for the 3 different types of microcapsules (X, Y and Z).

According to Low-Field NMR measurements, the perfume oil loading of the final powder reaches approximately 85% w/w.

Example 7

Preparation of a Dried Microcapsules According to the Invention Based on a Suspension of Core-Shell Microcapsules 70 g of the initial aqueous suspension of microcapsules X, Y or Z (prepared according to examples 1-3) is transferred into a separating funnel and concentrated by decantation, 35 g of water is then drained. Finally 14 g of water is removed from the remaining suspension by vacuum filtration, bringing the total water content below 50% w/w. The concentrated suspension obtained at that stage is a paste-like product.

0.21 g of fumed silica (Aerosil® R974 supplied by Evonik) and 21 g of the paste-like product are introduced into a shaker-mixer and allow to mix until obtaining free-flowing microcapsules. The free-flowing microcapsules are then transferred into a rotary pan, 53 g of maltodextrin (Glucidex 2 supplied by Roquette) and 0.074 g of flowing agent (Sipernat® supplied by Evonik) are incorporated into the rotary pan and blended for 1 hour to allow a homogeneous and complete drying of the microcapsules.

A free-flowing dried powder was obtained for the 3 different types of microcapsules (X, Y and Z).

The resulting powder mixture is used as such, according to Low-Field NMR measurements the perfume oil loading of the final powder reaches approximately 15% w/w.

Example 8

Preparation of a Dried Microcapsules According to the Invention Based on a Suspension of Core-Shell Microcapsules 70 g of the initial aqueous suspension of microcapsules X, Y or Z (prepared according to examples 1-3) is transferred into a separating funnel and concentrated by decantation, 35 g of water is then drained. Finally 14 g of water is removed from the remaining suspension by vacuum filtration, bringing the total water content below 50% w/w. The concentrated suspension obtained at that stage is a paste-like product.

1.68 g of magnesium stearate (technical grade Supplied by Sigma-Aldrich) and 21 g of the paste-like product are introduced into a shaker-mixer and allowed to mix until obtaining free-flowing microcapsules. The free-flowing microcapsules are then transferred into a rotary pan, 53 g of maltodextrin (Glucidex 2 supplied by Roquette) and 0.079 g of flowing agent (Sipernat® supplied by Evonik) are incorporated into the rotary pan and blended for 1 hour to allow a homogeneous and complete drying of the microcapsules.

A free-flowing dried powder was obtained for the 3 different types of microcapsules (X, Y and Z).

The resulting powder mixture is used as such, according to Low-Field NMR measurements the perfume oil loading of the final powder reaches approximately 14% w/w.

Example 9

Preparation of a Dried Microcapsules According to the Invention Based on a Suspension of Core-Shell Microcapsules 70 g of the initial aqueous suspension of microcapsules X, Y or Z (prepared according to examples 1-3) is transferred into a separating funnel and concentrated by decantation, 35 g of water is then drained. Finally 14 g of water is removed from the remaining suspension by vacuum filtration, bringing the total water content below 50% w/w. The concentrated suspension obtained at that stage is a paste-like product.

0.42 g of fumed silica (Aerosil® R974 supplied by Evonik) and 21 g of the paste-like product are introduced into a shaker-mixer and allow to mix until free-flowing microcapsules. The free-flowing microcapsules are then transferred into a rotary pan and mixed under air gas flow during one hour, then 21.4 g of maltodextrin (Glucidex 2 supplied by Roquette) and 0.05 g of flowing agent (Sipernat® supplied by Evonik) are incorporated into the rotary pan and blended for 1 hour to allow a homogeneous and complete drying of the microcapsules. A free-flowing dried powder was obtained for the 3 different types of microcapsules (X, Y and Z).

The resulting powder mixture is used as such, according to Low-Field NMR measurements the perfume oil loading of the final powder reaches approximately 25% w/w.

Example 10

Preparation of a Dried Microcapsules According to the Invention Based on a Suspension of Core-Shell Microcapsules 70 g of the initial aqueous suspension of microcapsules X, Y or Z (prepared according to examples 1-3) is transferred into a separating funnel and concentrated by decantation, 35 g of water is then drained. Finally 14 g of water is removed from the remaining suspension by vacuum filtration, bringing the total water content below 50% w/w. The concentrated suspension obtained at that stage is a paste-like product.

2.14 g of magnesium stearate (technical grade Supplied by Sigma-Aldrich) and 21 g of the paste-like product are introduced into a shaker-mixer and allowed to mix until obtaining free-flowing microcapsules. The free-flowing microcapsules are then transferred into a rotary pan and mix with 0.05 g of flowing agent (Sipernat® supplied by Evonik) under air gas flow during 4 hours, to allow a homogeneous and complete drying of the microcapsules.

A free-flowing dried powder was obtained for the 3 different types of microcapsules (X, Y and Z).

The resulting powder mixture is used as such, according to Low-Field NMR measurements the perfume oil loading of the final powder reaches approximately 85% w/w.

The invention claimed is:

1. A process for drying at room temperature or below room temperature a suspension of hydrogel microcapsules, said process comprising the steps of:
   (i) providing an aqueous suspension of hydrogel microcapsules, each hydrogel microcapsule comprising an oil phase containing a hydrophobic active ingredient;
   (ii) mixing the suspension obtained in step (i) with hydrophobic particles to obtain free-flowing microcapsules;
   (iii) drying the free-flowing microcapsules obtained in step (ii) by mixing the free-flowing microcapsules with a desiccant and/or by submitting the free-flowing microcapsules under a gas flow to obtain a dried free-flowing microcapsules powder; and
   (iv) optionally, sifting the dried microcapsules powder to remove excess desiccant.

2. The process according to claim 1, wherein the step (iii) comprises drying the free-flowing microcapsules obtained in step (ii) by mixing the free-flowing microcapsules with the desiccant.

3. The process according to claim 1, wherein the aqueous suspension is devoid of water-soluble carbohydrate carrier.

4. The process according to claim 1, wherein the hydrogel microcapsules are each in the form of a core-shell microcapsule, each microcapsule having a hydrogel shell and an oil-based core.

5. The process according to claim 1, wherein the ratio between the hydrophobic particles and the hydrogel microcapsules is between 0.001 and 0.15.

6. The process according to claim 1, wherein when the desiccant is used in step (iii), the ratio between the desiccant and the free-flowing microcapsules is between 0.1 and 10.

7. The process according to claim 1, wherein the hydrophobic particles are selected from the group consisting of treated silica, stearates, waxes, and mixtures thereof.

8. The process according to claim 1, wherein the desiccant is chosen from the group consisting of maltodextrin, starch, polyvinyl acetate, polyvinyl alcohol, dextrines, natural or modified starches, vegetable gums, pectins, xanthanes, alginates, carrageenans, cellulose derivatives, gelatines, Silicas, clays, activated charcoal, calcium sulfate, calcium chloride, molecular sieves, and mixtures thereof.

9. The process according to claim 1, wherein the hydrogel microcapsules are obtainable by a process selected from the group consisting of simple coacervation, complex coacervation, prilling, and interfacial polymerization.

10. The process according to claim 1, wherein the hydrophobic active ingredient is a perfume or a flavor.

11. The process according to claim 1, wherein the weight ratio between the hydrogel microcapsules and water is above 0.8.

* * * * *